(12) United States Patent
Glüsenkamp et al.

(10) Patent No.: US 6,602,692 B1
(45) Date of Patent: *Aug. 5, 2003

(54) METHOD FOR IMMOBILIZING BIOMOLECULES AND AFFINITY LIGANDS ON POLYMER CARRIERS

(76) Inventors: Karl-Heinz Glüsenkamp, Leanderbank 1, 45 239 Essen (DE); Gertrud Eberle-Adamkiewics, Im Stetefeld 30, 35 094 Lahntal (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/666,400
(22) PCT Filed: Dec. 1, 1994
(86) PCT No.: PCT/DE94/01422
§ 371 (c)(1),
(2), (4) Date: Jun. 6, 1996
(87) PCT Pub. No.: WO95/15983
PCT Pub. Date: Jun. 15, 1995

(30) Foreign Application Priority Data

Dec. 6, 1993 (DE) .......................................... 43 41 524

(51) Int. Cl.[7] .................. C12N 11/06; C12N 11/00; C07C 49/613; G01N 33/551
(52) U.S. Cl. ................... 435/181; 435/174; 435/180; 568/381; 436/524; 436/527; 436/528; 436/529; 436/530
(58) Field of Search .............................. 435/174, 180, 435/181; 568/381; 436/524, 527, 528, 529, 530

(56) References Cited

U.S. PATENT DOCUMENTS 4,560,504 A * 12/1985 Arnold ........................ 260/112
4,952,519 A * 8/1990 Lau ............................ 436/532

FOREIGN PATENT DOCUMENTS

WO          9012092          10/1990

OTHER PUBLICATIONS

Cuatrecasas et al , Affinity Chromatography, Methods in Enzymology, vol. XXII pp. 345–385, edited by William B. Jakoby, Academic Press, New York, 1971.*
Harlow E, Lane D, 1988. Antibodies: A laboratory Manual, Cold Spring Harbor: Cold Spring Harbor, 1988.*
Bioconjugate Chemistry; vol. 2, No. 3; May/Jun. 1991; pp 148–153.
Biosciences; vol. 46; 1991; pp 498–501.
Chemische Berichte; vol. 124—No. 5—May 1991; pp 1215–1221.

* cited by examiner

*Primary Examiner*—Maurie Baker
(74) *Attorney, Agent, or Firm*—R W Becker & Associates; R W Becker (57) ABSTRACT

In a method for immobilizing biomolecules and affinity ligands water insoluble matrices, having amino groups and selected from test tubes, microtiter plates, microscope slides, beads, membranes, resins, and filters, are reacted with a cyclobutene carboxylic acid derivative, such as cyclobutene carboxylic acid diester, cyclobutene carboxylic acid halide, cyclobutene carboxylic acid ester halide, cyclobutene carboxylic acid dialkoxyester, and cyclobutene carboxylic acid imidazole, as an activating compound in methanol and triethylamine to form active matrices with active groups. A protein containing at least one primary or secondary amino group, is dissolved and added to the matrices. The activated matrices and the dissolved protein are incubated at pH of 7–10 and a temperature of +4° C. to +60° C. in an aqueous buffer system, free of primary and secondary amines, to thereby immobilize the protein on the matrices.

10 Claims, 2 Drawing Sheets

FIG. 1

FIG. 1A

METHOD FOR IMMOBILIZING BIOMOLECULES AND AFFINITY LIGANDS ON POLYMER CARRIERS

BACKGROUND OF THE INVENTION

The present invention relates to new methods for immobilizing biomolecules such as, for example, different proteins, enzymes, monoclonal and polyclonal antibodies, cells, cell organelles, and tissue samples as well as affinity ligands, to a plurality of different polymer carriers as well as methods for manufacturing new affinity ligands reacting with amino groups. Affinity ligands in this context are to be understood to include, in the broadest sense, amino group containing biochemical probes, physiological indicators, antibiotics, enzyme inhibitors, chelates, lipids, tracers, oligopeptides, oligonucleotides, oligosaccharides, respectively, the corresponding monomer components. The chemical bond between the carriers and the ligands are amide-like bonds with a surprisingly high stability. A prerequisite for this coupling is that the polymer carrier as well as the ligand contain primary or secondary aliphatic amino groups, respectively, aromatic amino groups. A further advantage, in addition to the high stability of the bond, with respect to conventional immobilizing methods is the very gentle coupling chemistry which surprisingly allows to use, for example, only peripheral amino groups of proteins in a directed manner for the coupling. In comparison to previously known techniques the inventively used new immobilization results also in a substantial stabilization of many immobilized macromolecules such as immunoglobulins or enzymes so that they are partially protected against denaturation. The chemical "links" connecting to amino groups are derivatives of cyclobutene carboxylic acid (Formula I). Some derivatives of this acid are known (A. H. Schmidt, Synthesis, 1980, 961, K. H. Glusenkamp et al., Z. Naturforsch. C 1991, 46, 498, L. F. Tietze et al., Chem. Ber. 1991, 124, 1215).

SUMMARY OF THE INVENTION

Entirely new, however, is the use of this reagent for immobilizing amino group, containing molecules to polymer matrices, which must also contain an amino group, whereby the substituents $R^1$, $R^2$, A, B, PL, and PM of the general formula (I) have the meaning indicated in the description. Either PL and/or PM must be provided in dissolved form in order for immobilization to occur. A special advantage is that, for example, cyclobutene carboxylic acid diethyl esters can be reacted in a two-step reaction with amines to diamides. It is possible in this context to react first a polymer matrix (method A) or a ligand (method B) in a first step with the cyclobutene carboxylic acid diester. In both cases, in the second step a stable amide-analog bond is formed. It must be underscored that the reaction of the cyclobutene carboxylic acid diester with an amine to a monoamid is substantially faster than the subsequent reaction to the diamide. Furthermore, the cyclobutene carboxylic acid diester, cyclobutene carboxylic acid monoamide, and cyclobutene carboxylic acid diamide exhibit characteristic differences in their UV spectra. While cyclobutene carboxylic acid diester has a maximum at 250 nm, the monoester amide has a maximum at 272 nm, respectively, the diamides have a maximum at 290 to 300 nm with very high extinction coefficients. It is thus possible to monitor the degree of immobilization by UV spectroscopy, for example, due to the reduction of an activated ligand (cyclobutene carboxylic acid monoamide) in the reaction solution. Two surprising properties of the cyclobutene carboxylic acid derivatives must be underscored: 1. It has been shown that the cyclobutene carboxylic acid amide bond cannot be cleaved by conventional protease enzymes. This has important consequences for immobilized affinity ligands which are used for applications in biological systems because a substantially higher stability, respectively, life expectancy for this kind of covalent coupling in comparison to conventional amid or ester bonds is to be expected. 2. The surprisingly very selective coupling chemistry opens an unexpected, extremely broad range of reactions. For example, oligonucleotides with primary or secondary amines of any sequence and length can be reacted with cyclobutene carboxylic acid esters in a chemoselective manner without chemically changing the amino groups of the DNA bases. The thus produced oligonucleotides, activated with cyclobutene carboxylic acid groups, can subsequently be immobilized in a controlled manner on polymer matrices, for example, on membranes or latex surfaces. Furthermore, it is, for example, possible to selectively react the reactive oligonucleotides with marker molecules or probes such as, for example, digitoxigeninamine or dyes such as fluoresceine. The only requirement is that the marking molecule or probe is functionalized with amino groups. The surprisingly chemoselective reaction behavior of the cyclobutene carboxylic acid derivatives allows for the manufacture of novel compounds, which, for example, can may become important for the construction of chemosensors and biosensors. Surprisingly, it is, for example, possible to couple functionalized azamacrocycles or chelate forming compounds such as, for example, desferrioxamine B or also aminocyclodextrin with biological or synthetic membranes in a directed manner. It is also possible to activate, for example, lipids such as phosphatidyl ethanolamine derivites with cyclobutene carboxylic acid in order to attach in a second step any suitable marker molecule as, for example, chelates, dyes or also aminocyclodextrins, resulting in new lipids that can then, for example, be integrated in liposomes, can lead to lipisomes with favorable transport properties for active reagent or can lead to liposomes with a selective membrane transmissivity (channels). It is also possible, after activation of a matrix with cyclobutene carboxylic acid groups, to react any polyamine with the activated matrix. The thus directedly introduced further amino groups can then subsequently be again activated with cyclobutene carboxylic acid groups which are then, in turn, reacted with amines. The controlled chemical reaction at polymer surfaces (controllable in a directed manner by excess amounts of reagents) and the unique, stepped reaction behavior of the cyclobutene carboxylic acid diesters, respectively, cyclobutene carboxylic ester amides allows in this manner to generate novel functionalized polymers with comb, rotaxan or dendrimer structure. It is possible to generate extremely active surfaces with a high density of functional end groups which affect the physical and chemical properties in a considerable manner and, for example, are also able to stabilize very large molecules or even cells with a multitude of covalent or non-covalent bonds in a selective manner. On the other hand, it is possible in the same manner to bond in a directed manner low molecular compounds, after activation with cyclobutene carboxylic acid groups, with functionalized polymers.

The inventive method for manufacturing immobilized biomolecules and affinity ligands is primarily characterized by the steps of:

a) selecting a compound from amino group containing biomolecules and amino group containing affinity ligands and dissolving the selected compound;

b) reacting the selected and dissolved compound of step a) with a cyclobutene carboxylic acid derivative, selected from the group consisting of cyclobutene carboxylic acid diester, cyclobutene carboxylic acid halide, cyclobutene carboxylic acid dialkoxyester, cyclobutene carboxylic acid imidazole, in an inert solvent to form a cyclobutene carboxylic acid adduct;

c) dissolving a compound containing amino groups;

d) reacting the cyclobutene carboxylic acid adduct with the dissolved compound containing amino groups of step c) at a pH of 7–10 and a temperature of +4°C. to +60°C. in an aqueous buffer system, free of primary and secondary amines, to form an intermediate product with covalent cyclobutene carboxylic acid bridges; and e) reacting the intermediate product with covalent cyclobutene carboxylic acid bridges with a low molecular weight compound having active amino groups in an aqueous buffer system, free of primary and secondary amines, at a pH of 7–10.

The selected compound preferably contains at least one amino group selected from a primary amino group and a secondary amino group.

The selected compound is preferably a polymer.

The polymer is expediently a matrix.

The low-molecular weight compound preferably contains at least one amino group selected from a primary amino group and a secondary amino group.

The invention also relates to a method for manufacturing immobilized biomolecules and affinity ligands characterized by the following steps:

a) selecting a compound from amino group containing biomolecules and amino group containing affinity ligands and dissolving the selected compound;

b) reacting the selected and dissolved compound of step a) with a cyclobutene carboxylic acid derivative, selected from the group consisting of cyclobutene carboxylic acid diester, cyclobutene carboxylic acid halide, cyclobutene carboxylic acid dialkoxyester, cyclobutene carboxylic acid imidazole, in an inert solvent to form a cyclobutene carboxylic acid adduct;

c) dissolving a compound containing amino groups;

d) reacting the cyclobutene carboxylic acid adduct with the dissolved compound containing amino groups of step c) in an inert solvent to form an intermediate product with covalent cyclobutene carboxylic acid bridges; and e) reacting the intermediate product with covalent cyclobutene carboxylic acid bridges with a low molecular weight compound having active amino groups in an aqueous buffer system, free of primary and secondary amines, at a pH of 7–10.

The selected compound contains preferably at least one amino group selected from a primary amino group and a secondary amino group.

The selected compound is expediently a polymer.

The polymer is advantageously a matrix.

The low-molecular weight compound contains at least one amino group selected from a primary amino group and a secondary amino group.

The present invention also relates to another method for manufacturing immobilized biomolecules and affinity ligands characterized by the steps of:

a) reacting dissolved polymer matrices having amino groups with a cyclobutene carboxylic acid derivative selected from the group consisting of cyclobutene carboxylic acid diester, cyclobutene carboxylic acid halide, cyclobutene carboxylic acid ester halide, cyclobutene carboxylic acid dialkoxy ester, and cyclobutene carboxylic acid imidazole as an activating compound in an inert solvent to form active matrices with active groups;

b) dissolving a compound selected from biomolecules, containing at least one amino group selected from a primary amino group and a secondary amino group, and affinity ligands, containing at least one amino group selected from a primary amino group and a secondary amino group;

c) incubating the activated matrices with the dissolved compound of step b) at a pH of 7–10 and a temperature of +4° C. to +60° C. in an aqueous buffer system, free of primary and secondary amines; and d) reacting the incubated matrices of step c) with a low molecular weight compound having active amino groups in an aqueous buffer system, free of primary and secondary amines, at a pH of 7–10.

The low-molecular weight compound contains at least one amino group selected from a primary amino group and a secondary amino group.

The present invention further relates to a compound of the formula wherein

R$^1$ and R$^2$ are identical or different and are
hydrogen, cycloalkyl with 3 to 6 carbon atoms, linear or branched alkyl with up to 8 carbon atoms, substituted with halogen or linear or branched alkoxy with up to 6 carbon atoms or hydroxy;

phenyl or benzyl,
substituted with halogen, nitro group, cyano group, carboxy, linear or branched alkyl, alkoxy, acyl or alkoxycarbonyl with up to 6 carbon atoms, respectively, or a group of the formula —NR$^3$R$^4$, wherein
R$^3$ and R$^4$ are identical or different and are hydrogen or linear or branched alkyl with up to 6 carbon atoms, A is oxygen or sulfur,

B is oxygen or sulfur,

PL is, as a function of the meaning of PM, a compound functionalized with amino groups, PM is a watersoluble or waterinsoluble matrix of natural or synthetic origin with covalently bonded primary or secondary amino groups, cells, cell organelles, or tissue samples.

Preferably, PL is an enzyme, Protein A, Protein B, Protein G, immunoglobulin or their fragments or aminocyclodextrin.

The matrix preferably consists of cellulose, polystyrene, polypropylene, polycarbonate, or glass. The invention relates to compounds of the general formula (I)

(I)

wherein
R$^1$ and R$^2$ are identical or different and are: hydrogen, cycloalkyl with 3 to 6 carbon atoms or linear or branched alkyl with up to 8 carbon atoms, optionally substituted with halogen or linear or branched alkoxy with up to 6 carbon atoms, or hydroxy, phenyl or benzyl, optionally substituted with halogen, a nitro group, cyano group, carboxy group, linear or branched alkyl, alkoxy, acyl, or alkoxycarbonyl with respectively up to 6 carbon atoms, or a group of the formula —NR$^3$R$^4$, wherein R$^3$ and R$^4$ are identical or different and are hydrogen or linear or branched alkyl with up to 6 carbon atoms, A is oxygen or sulfur, B is oxygen or sulfur,

PL as a function of the respective meaning of PM is a protein or an enzyme, for example, alkaline phosphatase, β-galactosidase, T4 PN kinase, horseradish peroxidase, phospholipase C or, for example, proteinase such as papain, pepsin, proteinase K, carboxypeptidase, endoproteinase Arg-C, bromelain, collagenase, dipeptidyl peptidase IV, or nuclease, for example, RNase A, RNase T1, RNase T2, DNase I, Bal 31, or oxidase, for example, alcohol oxidase, glucose oxidase, or esterase, for example, phosphodiesterase I and II, or glucosidase, for example, β-glucoronidase, heparinas I, or lectin, for example, concanavalin A, or interleukin, or for a protein A or protein G or immunoglobulin of the type IgM, IgG, IgE, IgA and their fragments or other compounds functionalized with amino groups, for example, biochemical probes, physiological indicators, chelates, lipids, tracers, oligopeptides, oligonucleotides, oligosaccharides, respectively, the corresponding monomer components or antibiotics,

PM is a watersoluble or waterinsoluble matrix or natural or synthetic origin with covalently bonded primary or secondary amino groups in different embodiments (test tubes, microtiter plates, microscope slides, beads, membranes, resins, filters), which matrix, for example, is comprised of cellulose, polystyrene, polypropylene, polycarbonate, polymethacrylate, polyamide, or glass, or different cells, cell organelles, artificial liposomes, and tissue samples, or may have the meaning of PL.

The invention relates to preferably to compounds of the general formula (I) wherein R$^1$ and R$^2$ are identical or different and are: hydrogen, cycloalkyl with 3 to 4 carbon atoms or linear or branched alkyl with up to 6 carbon atoms, optionally substituted with halogen or linear or branched alkoxy with up to 4 carbon atoms, or hydroxy, phenyl or benzyl, optionally substituted with halogen, a nitro group, cyano group, carboxy group, linear or branched alkyl, alkoxy, acyl, or alkoxycarbonyl with respectively up to 4 carbon atoms, or a group of the formula —NR$^3$R$^4$, wherein R$^3$ and R$^4$ are identical or different and are hydrogen or linear or branched alkyl with up to 4 carbon atoms, A is oxygen or sulfur B is oxygen or sulfur,

PL as a function of the respective meaning of PM is a protein or an enzyme such as, for example, alkaline phosphatase, β-galactosidase, T4 PN kinase, horseradish peroxidase, phospholipase C or, for example, proteinase such as papain, pepsin, proteinase K, carboxypeptidase, endoproteinase Arg-C, bromelain, collagenase, dipeptidyl peptidase IV, or nuclease such as, for example, RNase A, RNase T1, RNase T2, DNase I, Bal 31, or oxidase such as, for example, alcohol oxidase, glucose oxidase, or esterase such as, for example, phosphodiesterase I and II, or glucosidase such as, for example, β-glucoronidase, heparinas I, or lectin such as, for example, concanavalin A or interleukin or a protein A or a protein G, or immunoglobulin of the type IgM, IgG, IgE, IgA and their fragments, or other compounds functionalized with amino groups as, for example, biochemical probes, physiological indicators, chelates, tracers, oligopeptides, oligonucleotides, oligosaccharides, respectively, the corresponding monomer components, or antibiotics,

PM is a watersoluble or waterinsoluble matrix in various embodiments (test tubes, microtiter plates, microscope slides, beads, membranes, resins, filters) of natural or synthetic origin with covalently bonded primary or secondary amino groups, which matrix is, for example, comprised of cellulose, polystyrene, polypropylene, polycarbonate, polymethacrylate, polyamide, or glass, or also different cells, cell organelles, artificial liposomes, and tissue samples, or may also have the meaning of PL.

The invention relates especially to compounds of the general formula (I) wherein R$^1$ and R$^2$ are identical or different and are: hydrogen, linear or branched alkyl with up to four carbon atoms, optionally substituted by halogen, or linear or branched alkoxy with up to 3 carbon atoms, or hydroxy, is benzyl, which is optionally substituted with halogen, a nitro group, cyano group, carboxy group, linear or branched alkyl, alkoxy, acyl, or alkoxycarbonyl with respectively up to 4 carbon atoms, or a group of the formula —NR$^3$R$^4$, wherein R$^3$ and R$^4$ are identical or different and are hydrogen or linear or branched alkyl with up to four carbon atoms, A, B is oxygen

PL as a function of the respective meaning of PM is a protein or an enzyme, as, for example, alkaline phosphatase, β-galactosidase, T4 PN kinase, horseradish peroxidase, phospholipase C or, for example, proteinase such as papain, pepsin, proteinase K, carboxypeptidase, endoproteinase Arg-C, bromelain, collagenase, dipeptidyl peptidase IV, or nuclease such as, for example, RNase A, RNase T1, RNase T2, DNase I, Bal 31, or oxidase such as, for example, alcohol oxidase, glucose oxidase, or esterase such as, for example, phosphodiesterase I and II, or glucosidase such as, for example, β-glucoronidase, heparinas I, or lectin such as, for example, concanavalin A or interleukin or Protein A, or Protein G, or biochemical probes, physiological indicators, chelates, tracers, oligopeptides, oligonucleotides, oligosacharides, respectively, the respective monomer components, or antibiotics, or immunoglobulin of the Type IgM, IgG, IgE, IgA and their fragments, a watersoluble or waterinsoluble matrix of natural or synthetic origin in various embodiments (test tubes, microtiter plates, microscope slides, beads, membranes, resins, filters) with covalently bonded primary or secondary amino groups, which matrix is, for example, comprised of cellulose, polystyrene, polypropylene, polycarbonate, polymethacrylate, polyamide, or glass, or various cells, cell organelles, artificial liposomes, and tissue samples, or may also have the meaning of PL.

The invention relates to immobilized biomolecules and affinity ligands characterized in that the immobilization reagents are cyclobutene carboxylic acid derivatives that bond the covalent biomolecules and affinity ligands to a matrix.

The invention also relates to immobilized biomolecules and affinity ligands characterized in that the immobilization reagent is a cyclobutene carboxylic acid derivative (I) having the general chemical structural formula as follows:

wherein $R^1$ and $R^2$ are identical or different and are:
  hydrogen, cycloalkyl with 3 to 6 carbon atoms or linear or branched alkyl with up to 8 carbon atoms, optionally substituted with halogen, or linear or branched alkoxy with up to 6 carbon atoms or hydroxy, phenyl or benzyl, optionally substituted with halogen, nitro group, cyano group, carboxy group, linear or branched alkyl, alkoxy, acyl, or alkoxycarbonyl with respectively up to 6 carbon atoms, or a group of the formula —$NR^3R^4$,
  wherein $R^3$ and $R^4$ are identical or different and are hydrogen or linear or branched alkyl with up to 6 carbon atoms,
A is oxygen or sulfur,
B is oxygen or sulfur, PL, as a function of the respective meaning of PM, is a protein or an enzyme, such as, for example, alkaline phosphatase, β-galactosidase, T4

PN kinase, horseradish peroxidase, phospholipase C or, for example, proteinase such as papain, pepsin, proteinase K, carboxypeptidase, endoproteinase Arg-C, bromelain, collagenase, dipeptidyl peptidase IV, or nuclease, such as, for example, RNase A, RNase Ti, RNase T2, DNase I, Bal 31, or oxidase, such as, for example, alcohol oxidase, glucose oxidase, or esterase such as, for example, phosphodiesterase I and II, or glucosidase, such as, forexample, β-glucuronidase, heparinase I, or lectin, such as, for example, concanavalin A, or interleukin, or a protein A or protein G or an immunoglobulin of the type IgM, IgG, IgE, IgA and their fragments or compounds functionalized with amino groups such as, for example, biochemical probes, physiological indicators, chelates, tracers, oligopeptides, oligonucleotides, oligosaccharides, respectively, the corresponding monomeric components, or antibiotics,

PM is a watersoluble or waterinsoluble matrix of a natural or synthetic origin in various embodiments (test tubes, microtiter plates, microscope slides, beads, membranes, resins, filters) with covalently bonded primary or secondary amino groups, such as, for example cellulose, polystyrene, polypropylene, polycarbonate, polymethacrylate, polyamide, or glass, or different cells, cell organelles, artificial liposomes, and tissue samples or may have the meaning of PL.

Preferably, the biomolecules and affinity ligands which must contain at least one primary or secondary amino group, are activated with a cyclobutene carboxylic acid diester or cyclobutene carboxylic acid halide to form a cyclobutene carboxylic acid adduct and are subsequently reacted with any suitable matrix which must contain primary or secondary amino groups, under formation of covalent cyclobutene carboxylic acid bridges.

Biotin derivatives such as preferably biocytin are reacted according to the inventive method with cyclobutene carboxylic acid diethyl esters in ethanol or dimethylformamide in the presence of triethyl amine or pyridine as a base at room temperature to the adduct AL1 and subsequently are reacted preferably with polymethacrylate with aliphatic amino groups (particle size: 65 µ, 100 µmol/ml amine, AF-amino-650 M, Tosohaas in ethanol or dimethylformamide in the presence of triethylamine or pyridine as a base or in aqueous buffer systems (carbonate, borate) at pH 9.0 at room temperature to form the immobilized affinity ligand ALa as a compound of the general formula (I): $R^1$, $R^2$=H; A,B=O; PM=polymethacrylate; PL=bicytinyl.

Antibiotics, preferably daunomycin, are reacted according to the present invention with cyclobutene carboxylic acid diethyl ester and ethanol or dimethylformamide in the presence of triethylamine or pyridine as a base at room temperature to the adduct AL2 and subsequently are reacted, preferably with polymethacrylate, functionalized with aliphatic amino groups (particle size: 65 µ, 100 µmmol/ml amine, AF-amino-650 M, Tosohaas) in ethanol or dimethylformamide in the presence of triethylamine or pyridine as a base or in aqueous buffer systems (carbonate, borate) at pH 9.0 at room temperature to form the immobilized antibiotic ALb as a compound of the general formula (I): $R^1$, $R^2$=H; A, B=O; PM=polymethacrylate; PL=daunomycinyl

Oligopeptides, as preferably glutathione, are reacted according to the present invention with cyclobutene carboxylic acid diethyl ester in ethanol or dimethylformamide in the presence of triethylamine or pyridine as a base at room temperature to the adduct AL3 and subsequently reacted with polymethacrylate functionalized with aliphatic amino groups (particle size: 6µ, 100 µmol/ml amine, AF-amine-650 M, Tosohaas) in ethanol or dimethylformamide in the presence of triethyl amine or pyridine as a base or also in aqueous buffer systems (carbonate, borate) at pH 9.0 at room temperature to form the immobilized affinity ligand ALc as a compound of the general formula (I): $R^1$, $R^2$=H; A, B =O; PM=polymethacrylate; PL=gluthationyl.

Penicillin compounds, preferably amoxicillin, is reacted according to the present invention with cyclobutene carboxylic acid diethyl ester in ethanol or dimethylformamide in the presence of triethylamine or pyridine as a base at room temperature to the adduct AL4 and

-continued subsequently preferably is reacted with polymethacrylate, functionalized with aliphatic amino groups (particle size 65μ, 100 μmol/ml amine, AF-amino-650 M, Tosohaas) in ethanol or dimethylformamide in the presence of triethylamine or pyridine as a base or also in aqueous buffer systems (carbonate, borate) at pH 9.0 at room temperature to form the immobilized affinity ligand ALd as a compound of the general formula (I): $R^1$, $R^2$=H; A, B=O; PM=polymethacrylate; PL=amoxicillyl.

Antimycotics such as preferably amphotericin B are reacted according to the present invention with cyclobutene carboxylic acid diethyl ester in ethanol or dimethylformamide in the presence of triethylamine or pyridine as a base at room temperature to form the adduct AL5 and subsequently reacted preferably polyamides functionalized with amino groups (preferably Biodyne A, Pall) in ethanol or dimethylformamide in the presence of triethylamine or pyridine as a base or in aqueous buffer systems (carbonate, borate) at pH 9.0 at room temperature to form the immobilized affinity ligand ALe as a compound of the general formula (I): $R^1$, $R^2$=H; A, B=O; PM=polyamide; PL=amphotericinyl B.

Chelate forming compounds such as preferably iron ion-selective desferrioxamine B are reacted according to the present invention with cyclobutene carboxylic acid diethyl ester in ethanol or dimethylformamide in the presence of triethylamine or pyridine as a base at room temperature to form the adduct AL6 and subsequently reacted preferably with polyamides, which are functionalized with aliphatic amino groups, in ethanol or dimethylformamide in the presence of triethylamine or pyridine as a base or in aqueous buffer systems (carbonate, borate) at pH 9.0 at room temperature to form the immobilized affinity ligand ALf as a compound of the general formula (I): $R^1$, $R^2$=H; A, B=O; PM=polyamide; PL=desferrioxaminyl B.

X = H Desferrioxamin B

Amino-functionalized crown ethers such as preferably 2-aminomethyl-12-crown-4 are reacted according to the present invention with cyclobutene carboxylic acid diethyl ester in ethanol or dimethylformamide in the presence of triethylamine or pyridine as a base at room temperature to form the adduct AL7 and subsequently reacted preferably with a polyamide membrane (Byodyne A, Pall GmbH) in ethanol or dimethylformamide in the presence of triethylamine or pyridine as a base or in aqueous buffer systems (carbonate, borate) at pH 9.0 at room temperature to form the immobilized affinity ligands ALg as a compound of the general formula (I): $R^1$, $R^2$=H; A, B=0; PM=polyamide; PL=2-aminomethyl-12-crown-4.

Chelate forming compounds such as preferably substituted DOTA are reacted according to the present invention with cyclobutene carboxylic acid diethyl ester in ethanol or dimethylformamide in the presence of triethylamine or pyridine as a base at room temperature to form the adduct AL8 and subsequently reacted with a polyamide membrane functionalized with amino groups (Biodyne A, Pall) in ethanol or dimethylformamide in the presence of triethylamine or pyridine as a base or in aqueous buffer system (carbonate, borate) at pH 9.0 at room temperature to form the immobilized affinity ligand ALh as a compound of the general formula (I): $R^1$, $R^2$=H; A, B=O; PM=polyamide; PL=aminobutyl-DATA.

Amino sugars such as preferably aminocyclodextrin are reacted according to the present invention with cyclobutene carboxylic acid diethyl ester in ethanol or dimethylformamide in the presence of triethylamine or pyridine as a base at room temperature to the adduct AL9 and subsequently reacted with polyacrylate functionalized with aliphatic amino groups (particle size: 65µ, 100 µmol/ml amine; AF-amino-650 M, Tosohaas) in ethanol or dimethylformamide in the presence of triethylamine or pyridine as a base or in aqueous buffer systems (carbonate, borate) at pH 9.0 at room temperature to form the immobilized affinity ligand ALi as a compound of the general formula (I): $R^1$, $R^2$=H; A, B=O; PM=polymethacrylate; PL=aminocyclodextrinyl.

Amino substituted DNA components such as 3-aminopropyl-adenine are reacted according to the present invention with cyclobutene carboxylic diethyl ester and ethanol or dimethylformamide in the presence of triethylamine or pyridine as a base at room temperature to form the adduct AL10 and subsequently reacted preferably with glass beads which are functionalized with amino groups (aminopropyl glass, Sigma) in ethanol or dimethylformamide in the presence of triethylamine or pyridine as a base or in aqueous buffer systems (carbonate, borate) at pH 9.0 at room temperature to form the immobilized affinity ligand ALj as a compound of the general formula (I): $R^1$, $R^2$=H; A, B=O; PM=glass beads; PL=3-propyl-(-3-yl)-adenine.

Dyes or indicators such as preferably amino-substituted fluorescein derivatives are reacted according to the present invention with cyclobutene carboxylic acid diethyl ester in ethanol or dimethylformamide in the presence of triethylamine or pyridine as a base at room temperature to form the adduct AL11 and subsequently reacted preferably with glass beads functionalized with aliphatic amino groups in ethanol or dimethylformamide in the presence of triethylamine or pyridine as a base or in aqueous buffer systems (carbonate, borate) at pH 9.0 at room temperature to form the immobilized affinity ligands ALk as a compound of the general formula (I): $R^1$, $R^2$=H; A, B=O; PM glass beads; PL=5-((5-pentenyl)-thioureidyl)fluorescein.

Steroids such as, for example, aminodigitoxigenin are reacted according to the present invention with cyclobutene carboxylic acid diethyl ester in ethanol or dimethylformamide in the presence of triethylamine or pyridine as a base at room temperature to form the adduct AL12 and subsequently reacted with oligonucleotides functionalized with amino groups such as preferably 5'-amino-polydG in ethanol or dimethylformamide in the presence of triethylamine or pyridine as a base or in aqueous buffer systems (carbonate, borate) at pH 9.0 at room temperature to form the immobilized affinity ligand ALh as a compound of the general formula (I): $R^1$, $R^2$=H; A, B=O; PM=5'-yl-polydG; PL=digitoxigenyl.

Amino-functionalized oligonucleotides such as preferably 5'-Amino-poly(dG)$_{12}$ are reacted according to the present invention in ethanol or dimethylformamide in the presence of triethylamine or pyridine as a base at room temperature or in aqueous buffer systems of pH 7.5 with cyclobutene carboxylic acid diethyl ester to form the adduct AL13 and subsequently reacted preferably with polyamide membranes functionalized with aliphatic amino groups (Biodyn A, Pall) in ethanol or dimethylformamide in the presence of triethylamine or pyridine as a base or in aqueous buffer systems (carbonate, Borate) at pH 9.0 at room temperature to form the immobilized affinity ligand ALm as a compound of the general formula (I): $R^1$, $R^2$=H; A, B=O; PM=polyamide; PL=5'-yl-poly(dG)$_{12}$.

Polymer matrices or affinity ligands, which contain primary or secondary amino groups, are reacted according to the present invention with cyclobutene carboxylic acid diester, cyclobutene carboxylic acid halide, or cyclobutene carboxylic acid ester halide as activating reagents under formation of active groups to activated matrices or activated affinity ligands.

Biomolecules and affinity ligands PL and/or PM, which must contain at least one primary or secondary amino group, are reacted according to the present invention with a selected activated matrix under formation of a covalent bond or a plurality of stable covalent bonds.

A polymer matrix or affinity ligands, which contain primary or secondary amino groups, are reacted according to the present invention with cyclobutene carboxylic acid diesters, cyclobutene carboxylic acid halides, or cyclobutene carboxylic acid ester halide at 0C. to +100° C., preferably at +100 C. to +60° C.

The reaction is preferably carried out in a conventional organic solvent, that will not change during reaction, with less than molar or greater than molar amounts with respect to the amino groups.

The activation is carried out in the presence of organic bases, preferably triethylamine or pyridine, and these bases are added in an amount of 1 mol to 100 mol, preferably 1 mol to 10 mol, relative to 1 mol of the compound of the general formula (I).

The reaction time varies as a function of the selected reaction components and the reaction temperature, whereby times of 0.1 to 10 hours are preferred.

As a polymer matrix or as an affinity ligand all synthetic as well as natural compounds are suitable which contain covalent primary or secondary amino groups.

As a reaction medium all aqueous buffer system are suitable such as preferably phosphate, citrate, borate, carbonate, or mixtures thereof.

The concentration of the molecules to be conjugated can vary in wide ranges and is preferably for proteins to be coupled between 0.01 and 50 mg/ml.

The reaction can be performed in a temperature range of +4° C. to +60° C.

The pH value during the coupling reaction may be between 7 and 10.

The reaction time varies as a function of the selected reaction components, the reaction temperature, and the pH value and is normally between 0.1 and 50 hours.

The remaining active cyclobutene carboxylic acid groups after immobilization are deactivated according to the present invention with low molecular weight compounds that must contain at least one primary or secondary amino group.

As a blocking medium all aqueous buffer systems are suitable.

The concentration of the reactive groups for blocking can vary within wide ranges and is preferably for amino acids within a range between 0.01 and 100 mg/ml.

The reaction temperature for blocking can be within a temperature range of +4° C. to +60° C.

The pH value during the blocking reaction is between pH 7 and 10.

The reaction time as a function of the selected blocking compounds, the reaction temperature and the pH value is preferably between 0.1 and 50 hours.

BRIEF DESCRIPTION OF THE DRAWING

The only schematic drawing shows a flow diagram for the various reaction steps of the present invention.

DESCRIPTION OF PREFERRED EMBODIMENTS

The inventive method will be explained in the following with the aid of the schematic representation (FIG. 1) without intending to limit the method in any way. The method for immobilizing is comprised of a method A and B carried out in a total of three steps, respectively:

IA. Activation

Figure 1:
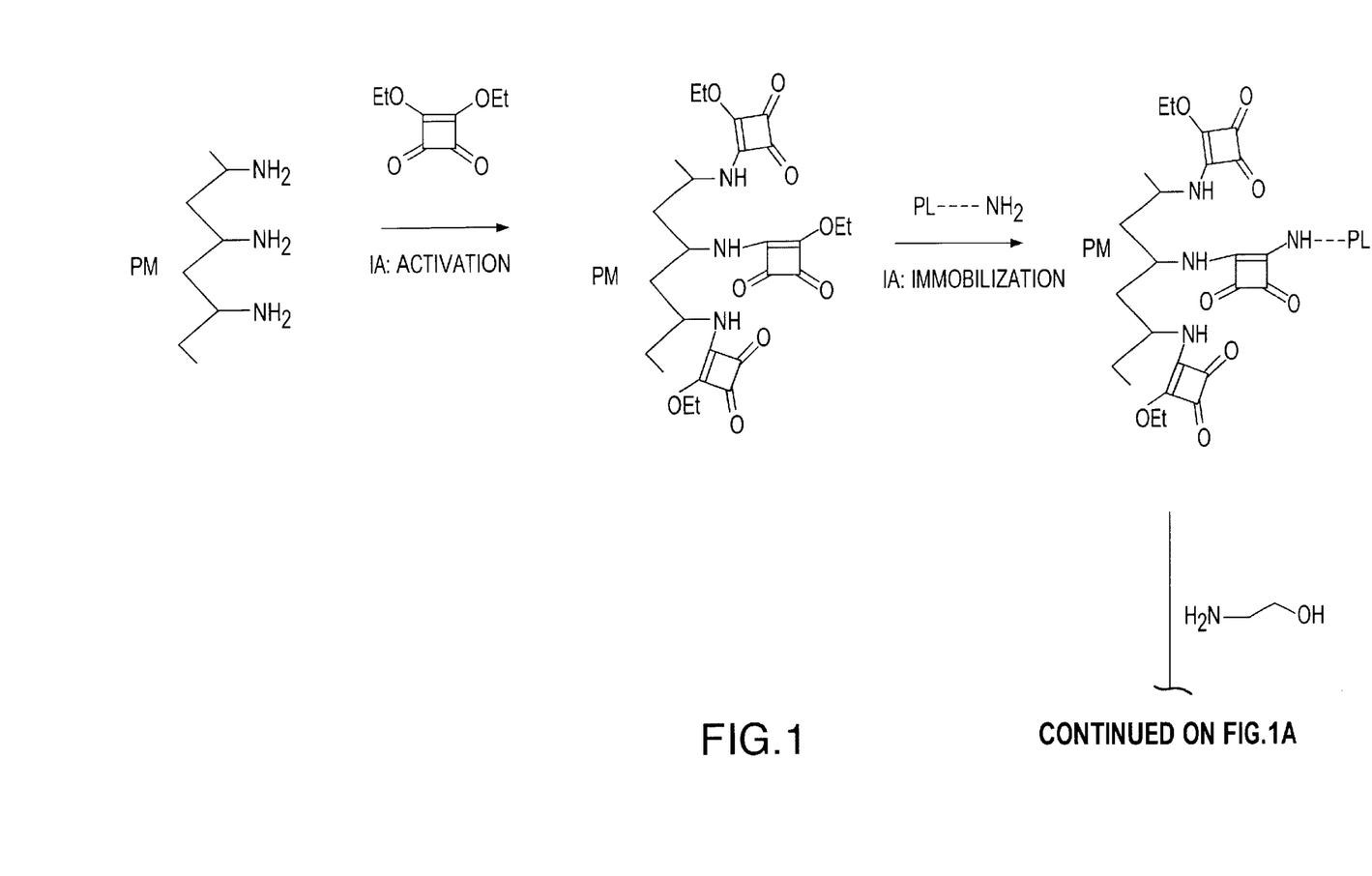
Figure 1A:
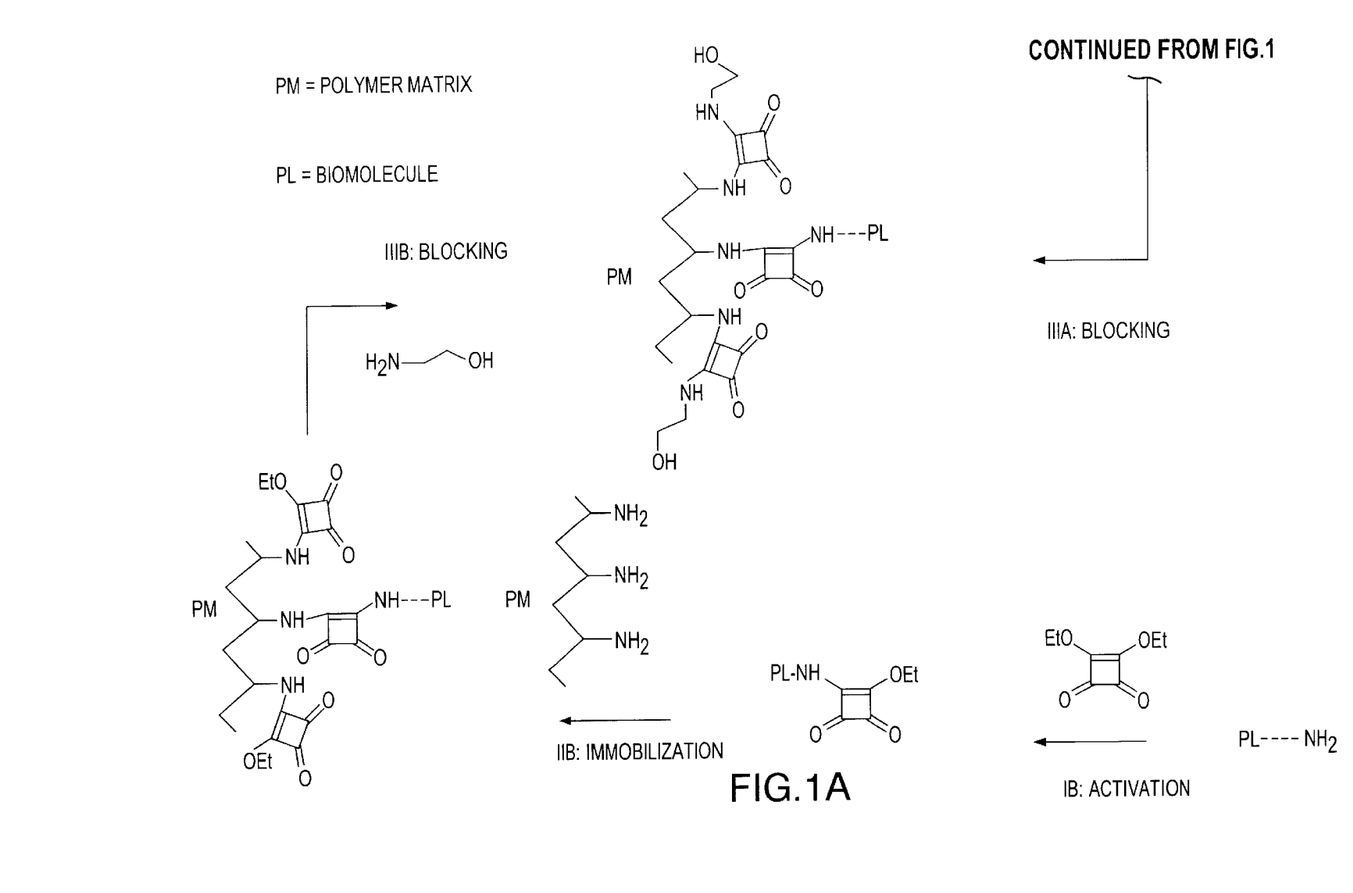

An amino group carrying matrix —PM—NH$_2$— is reacted in an inert solvent with a selected cyclobutene carboxylic acid dialkoxyester (such as, for example, dimethylester, diethylester or dibutylester) or with a cyclobutene carboxylic acid halide or cyclobutene carboxylic acid imidazolide, optionally in the presence of an organic base, to an activated matrix (FIG. 1).

The cyclobutene carboxylic acid dialkoxyester or the cyclobutene carboxylic acid halide can be reacted depending on the desired degree of activation in less than molar ratio up to a large excess relative to the amino groups of the matrix to be activated (for example, 0.1 to 100). In the latter case reaction will be complete. It is especially advantageous in connection with this activation method that a complete recovery of the unreacted cyclobutene carboxylic acid derivative is easily possible.

As inert solvents conventional organic solvents are suitable which will not change under the aforementioned reaction conditions. As. a function of the employed cyclobutene carboxylic acid derivative, these include preferably alcohols such as ethanol, methanol, propanol, butanol, or ether such as diethylether, butylmethylether, dioxane, or tetrahydrofurane, or hydrocarbons such as benzane, tolurane, xylene, or hexane or amides such as dimethylformamide, or hexamethyl phosphoric acid triamide, or nitrile such as acetonitrile or sulfoxide such as dimethyl sulfoxide, or chetones such as acetone or halogenated hydrocarbons such as chloroform or dichloromethane. It is also possible to use mixtures of the aforementioned solvents. Especially preferred is ethanol or diethyl ether.

Organic bases such as, for example, triethylamine, tripropylamine, pyridine, piperidine, N,N-dimethylaminopyridine, N-methylimidazole or picoline are used in general. Preferred is triethylamine.

The base is in general added in an amount of 1 mol to 100 mol, preferably in the range of 1 mol to 10 mol, relative to 1 mol of the compounds of the general formula (I).

The reaction is carried out in a temperature range of 0° C. to +100° C., preferably within a range of +4° C. to +60° C.

In general, the reaction is carried out at ambient pressure. It is also possible to perform the reaction at increased or lowered pressure (for example, from 0.5 to 5 bar).

The reaction time varies as a function of the selected reaction components and the reaction temperature.

IIA. Immobilization

The matrix thus activated with cyclobutene carboxylic acid esters is subsequently coupled in an aqueous buffer system, which optionally contains organic solvents, with amino group carrying, for example, polymer compounds to stable conjugated compounds whereby one or more stable covalent bonds may be formed.

As a reaction medium any aqueous buffer system is suitable, as long as they are free of primary and secondary amines, such as, for example, phosphate, citrate, borate, carbonate, tris amine or other mixtures. The concentration can be varied within a wide ranges, for example, from 0.01 to 5 mol, preferably it is 0.1 mol.

The concentrations of the molecules to be conjugated can vary in wide ranges and is, for example, for proteins to be coupled between 0.01 and 50 mg/ml.

The reaction takes place in a temperature range of +4° C. to +60° C, preferably in a range of +4° C. to +40° C.

The reaction is, in general, carried out at ambient pressure. It is also possible to perform the reaction at increased or lowered pressure (for example, from 0.5 to 5 bar).

The pH value of the coupling reaction can be between pH 7–10, preferably it is pH 9.

The reaction time varies as a function of the selected reaction components, the reaction temperature and the pH value and is, in general, 0.1–50 hours.

IIIA. Blocking of the Remaining Reactive Groups of the Activated Polymer Carrier The inventive mild method proves to be especially advantageous relative to other immobilization methods because it allows for deactivation of the remaining unreacted active groups in a directed manner. For blocking the remaining active groups, low molecular compounds with active amino groups such as, for example, monomer or oligomer amino acids, amino alcohols as, for example, ethanol amine or diethanolamine, amino ether as, for example, polyethyleneglycol amine or amino sugars, for example, glucosamine are suitable. In this manner it is possible to additionally covalently bond in a directed manner positive, negative, hydrophilic, hydrophobic, or amphiphatic groups of different size onto the polymer matrix. It is thus possible to modulate, respectively, to stabilize the biochemical, immunochemical, or enzymatic reactions or activities.

As a blocking medium all aqueous buffer system are suitable as long as they are free of primary and secondary amines, such as, for example, phosphate, citrate, borate, carbonate, tris amine or also mixtures of the aforementioned systems. The concentrations can vary in wide ranges, for example, from 0.01 to 5 mol, preferred is 0.1 mol.

The concentration of the groups to be conjugated can vary in wide ranges and is, for example, for amino acids between 0.01 and 100 mg/ml.

The reaction takes place within a temperature range of +4° C. to +60° C., preferably in a range of +4° C. to +40° C.

The reaction is, in general, performed at ambient pressure. It is also possible to carry out the reaction at increased or lowered pressure (for example, from 0.5 to 5 bar).

The pH value of the blocking reaction can be between pH 7–10, preferably it is pH 9.

The reaction time varies as a function of the selected reaction components, the reaction temperature, and the pH value and is, in general, 0.1 to 50 h.

IB. Activation

An amino group carrying affinity ligand or biomolecule —PL—NH$_2$— is activated in a solvent with any desired cyclobutene carboxylic acid dialkoxyester (as, for example, dimethylester, diethylester or dibutylester) or with a cyclobutene carboxylic acid halide or cyclobutene carboxylic acid imidazol optionally in the presence of an organic base (FIG. 1).

The cyclobutene carbocxylic acid dialkoxy ester or the cyclobutene carboxylic acid halide can be added depending on the desired degree of activation in a less than molar ratio or in excess molar ratio to the amino groups of the affinity ligands or biomolecules to be activated (for example 0.1 to 100). In the latter case reaction will be complete.

As inert solvents any conventional organic solvent is suitable which does not change under the aforementioned reaction conditions. As a function of the cyclobutene carboxylic acid derivative used, these include preferably alcohols such as ethanol, methanol, propanol, butanol, or ethers such as diethylether, butylmethylether, dioxane or tertrahydrofurane, or hydrocarbons such as benzene, toluene, xylene, or hexane, or amides such as dimethylformamide, or hexamethyl phosphoric acid triamide, or nitrile such as acetonitrile, or sulfoxide such as dimethyl sulfoxide, orketones such as acetone, or halogenated hydrocarbons such as chloroform or dichloromethane. It is also possible to use mixtures of the aforementioned solvents. It is also possible to use mixtures of the named solvents. Especially preferred are ethanol or diethyl ether. It is also possible to carry out the activation in aqueous buffer systems at different pH values of 5–9. Preferred are pH values of 6–7.5. It is also possible to mix the buffer systems with organic solvents.

In general, organic bases such as, for example, triethylamine, tripropylamin, pyridine, N,N-dimethylaminopyridine, N-methylimidazol, imidazole or picoline are used as bases. Preferred is triethylamine.

The base is, in general, used in an amount of 1 mol to 100 mol, preferably 1 mol to 10 mol, relative to 1 mol of the compound of the general formula (I).

The reaction is carried out in a temperature range of 0° C. to +100° C., preferably in a range of +4° C. to +60° C.

The reaction is in general performed at ambient pressure. It is also possible to perform the reaction at increased or lowered pressure (for example, from 0.5 to 5 bar).

The reaction time varies as a function of the selected reaction components and the reaction temperature.

IIB. Immobilization

The affinity ligands activated in the aforementioned manner with cyclobutene carboxylic acid groups are subsequently coupled in an aqueous buffer system, that may optionally contain organic solvents, or in organic solvents with amino group carrying, for example, polymer compounds to stable conjugated compounds whereby one or more stable covalent bonds may be formed.

As the aqueous reaction medium any aqueous buffer system is suitable as long as it is free of primary and secondary amines such as, for example, phosphate, citrate, borate, carbonate, tris amine or also mixtures. The concentration can vary in wide ranges, for example from 0.01 to 5 molar, preferred is 0.1 molar.

As inert organic solvents conventional organic solvents are suitable which will not change under the aforementioned reaction conditions. As a function of the used cyclobutene carboxylic acid derivative these include preferably alcohols, such as ethanol, methanol, propanol, butanol, or ether such as diethylether, butylmethylether, dioxane or tertrahydrofurane, or hydrocarbons such as benzene, toluene, xylene, or hexane, or amides such as dimethylformamide, or hexamethyl phosphoric acid triamide, or nitrile such as acedonitrile, or sulfoxide such as dimethyl sulfoxide, or ketones such as acetone, or halogenated hydrocarbons such as chloroform or dichloromethane. It is also possible to use mixtures of the aforementioned solvents. Especially preferred is ethanol or dimethylsulfoxide or DMF.

The concentrations of the conjugated molecules can vary in wide ranges and is preferably for the affinity ligands to be coupled between 0.01 and 50 mg/ml.

The reaction takes place in a temperature range of +4° C. to +60° C., preferably in a range of +4° C. to +40° C.

The reaction as, in general, performed at ambient pressure.

However, it is also possible to carry out the reaction at increased or lowered pressure (for example, from 0.5 to 5 bar).

The pH value of the coupling reaction can be between pH 7–10, preferred is a pH value of 9.

The reaction time varies as a function of the selected reaction components, the reaction temperature, and the pH value and is usually between 0.1–50 hours.

IIIA. Blocking of the Remaining Reactive Groups of the Activated Polymer Carrier.

The conditions are identical to the ones described under IIIA.

EXAMPLES

1. Immobilization of Cells and Tissue Samples on Microscope Slides a) Activation of the Microscope Slide Microscope slides are aminopropylated according to standard methods. Onto the thus prepared microscope slides a 10% solution of cyclobutene carboxylic acid diethylester (Aldrich) in ethanol (1% triethylamine) is placed and incubated at room temperature for 10 hours. Subsequently, the microscope slide is intensively washed with ethanol, then washed with a phosphate buffer of pH 6.0, and subsequently dried in air. The thus activated glass surface can be kept for an unlimited time at +4° C. in a saturated ethanol atmosphere.

b) Immobilization of Poly-D-lysin

The previously activated microscope slides are incubated for 24 hours in a solution of poly-D-lysine (sigma, molecular weight 1000–4000, 5 mg/ml), in 150 mM borate (pH 9.0). Subsequently, they are washed intensively with borate at pH 9, phosphate at pH 7, and subsequently with increasing amounts of ethanol up to 100% and air dried. Instead of polylysine other polyamines can be used as well.

c) Second Activation with Cyclobutene Carboxylic Acid Diester (Activation of the Aminogroups of Lysine)

The microscope slides previously treated with poly-D-lysine are introduced into a 10% solution of cyclobutene carboxylic acid diethylester in ethanol (1% triethylamine) and are again incubated at room temperature for 10 hours. Subsequently, they are washed intensively with ethanol, finally with a phosphate buffer at pH 6.0, and subsequently are air-dried.

d) Fixation of Cells on Activated Microscope Slides

Serum free cells (for example, mouse myelomacells) are applied with a minimal amount of isotonic buffer (borate, pH 8.0) onto the microscope slides, optionally slightly centrifuged, and subsequently incubated at +37° C. for an hour. Subsequently, the microscope slides are treated for another hour with 200 mM lysine (pH 8–8.5) and are subsequently intensively washed with PBS (pH 7.4). The thus immobilized cells form a gap-free, very stable cell layer on the microscope slide.

2. Immobilization of Protein A on AF-amino Toyopearl 650 N (Tosohaas)

a) Activation of the Gel with Cyclobutene Carboxylic Acid Diester.

25 g of polyacrylate functionalized with aliphatic amino groups (particle size: 65 µ, 100 µmol/ml amine, AF-amino-650 M, Tosohaas) is intensively washed with distilled water and subsequently treated with ethanol (absolute). 2 g (0.018 mol) of cyclobutene carboxylic acid diethyl ester (Aldrich) is dissolved in 4 ml ethanol (absolute), added to 25 g of pretreated polyacrylate with aliphatic amino groups to which is introduced 1000 g (0.068 mol) of triethylamine. The solution is filtered after 10 hours and the residue intensively washed with ethanol.

b) Immobilization of Protein A 1 g of the activated colorless gel is incubated with 16 mg protein A (Sigma) in 1.5 ml borate buffer (pH 9.2) at room temperature for 12 hours. With the aid of UV spectroscopy and gel filtration the kinetics of the immobilization reaction is determined. After 12 hours no protein can be detected in the solution. The gel is subsequently washed with borate buffer (pH 9.2) and incubated with 200 mM ethanolamine (pH 9.2) for 5 hours in order to block the remaining reactive groups.

Subsequently, the gel is again washed with buffer (PBS, pH 7.4) and can then be used for cleaning of antibodies (bonding capacity: approximately 30 mg IgG/ml gel).

3. Immobilization of Glutathione on AF-Amino Toyopearl 650 N (Polymethacrylate Matrix, Tosohaas)

Method A: 20 g of the activated colorless gel are incubated with 0.1 g (0.00032 mol) glutathione (Sigma) in 30 ml ethanol at room temperature with addition of 2000 μl triethylamine as a base for 12 hours. After 12 hours no glutathione can be detected in solution (HPLC analysis). The remaining active groups of the gel are deactivated by addition of 5000 μl of ethanol amine. After 2 hours the gel is washed with methanol, and subsequently equilibration is performed with PBS (0.01% azide).

Method B: 0.100 g (0.00032 mol) glutathione (Sigma) is completely reacted in 2 ml ethanol/DMSO with 0.0553 g of cyclobutene carboxylic acid diethyl ester (Aldrich) in the presence of 0.1 ml triethylamine for 10 hours at room temperature to form the adduct AL3 (see claims). This solution is then incubated on 20 g of aminopolymethacrylate (Tosohaas) with addition of 2 ml triethylamine as a base for 12 hours at room temperature. Subsequently, no AL3 can be detected in the solution (UV spectroscopy). The remaining active groups at the gel are deactivated by addition of 5000 μl ethanolamine. After 2 hours the gel is washed with methanol, and subsequently equilibration is performed with PBS (0.01% Azid).

4. Manufacture of a Novel, Activated Matrix for Covalent Immobilization of Different Biomolecules and Affinity Ligands (Hydra-link, Q-link, Polyp, Hydra, Medusa)

10 g of the gel activated according 2.a) are reacted with 1 g (0.0043 mol) polypropylene glycol-bis-(2-aminopropylether) (molecular weight 230, Fluka) in 5 ml methanol and carefully shaken for 24 hours at room temperature in the presence of triethylamine. Subsequently, methanol is used for washing, and 1 g (0.009 mol) of cyclobutene carboxylic acid dieihylester (Aldrich) in 4 ml methanol are added to the gel wet with methanol, and 0.1 g (0.0068 mol) triethylamine are added. After 10 hours the gel is filtered, washed intensively with methanol, and the activated polymethacrylate matrix thus obtained has a very hydrophilic comb structure which at the heads is provided with reactive cyclobutene carbxylic acid groups.

These activated gels are substantially stable in their methanol-wet state for an unlimited period of time. These activation methods are suitable for many amino group containing matrices. Furthermore, the chain length of the hydrophilic spacer can be systematically varied. The bonding capacity of these activated matrices are very high and, in the case of immobilization with glutathione, is 180 mg/g of gel.

These novel surfaces chemically altered according to this method are especially suitable for immunoaffinity chromatagraphic problems and also for enzymatic reactions which are favorably affected by these hydrophilic surfaces.

The present invention is, of course, in no way restricted to the specific disclosure of the specification and drawings, but also encompasses any modifications within the scope of the appended claims.

What is claimed is:

1. A method for immobilizing biomolecules and affinity ligands, said method comprising the steps of:
   a) reacting water insoluble matrices, having amino groups and being selected from the group consisting of test tubes, microtiter plates, microscope slides, beads, membranes, resins, and filters, with a cyclobutene carboxylic acid derivative, selected from the group consisting of cyclobutene carboxylic acid diester, cyclobutene carboxylic acid halide, cyclobutene carboxylic acid ester halide, cyclobutene carboxylic acid dialkoxyester, and cyclobutene carboxylic acid imidazole, as an activating compound in methanol in the presence of triethylamine to form active matrices with active groups;
   b) dissolving a protein containing at least one primary or secondary amino group and adding the protein to the activated matrices;
   c) incubating the activated matrices and the protein of step b) at a pH of 7–10 and a temperature of +4° C. to +60° C. in an aqueous buffer system, free of primary and secondary amines, to thereby immobilize the protein of step b) on the matrices.

2. A method according to claim 1, further including the steps of:
   d) reacting the matrices of step c) with a cyclobutene carboxylic acid derivative, selected from the group consisting of cyclobutene carboxylic acid diester, cyclobutene carboxylic acid halide, cyclobutene carboxylic acid ester halide, cyclobutene carboxylic acid dialkoxyester, and cyclobutene carboxylic acid imidazole, as an activating compound in methanol in the presence of triethylamine to reactivate the matrices with active groups;
   e) dissolving a protein containing at least one primary or secondary amino group and adding the protein to the reactivated matrices of step d);
   f) incubating the reactivated matrices and the protein of step e) at a pH of 7–10 and a temperature of +4° C. to +60° C. in an aqueous buffer system, free of primary and secondary amines, to thereby immobilize the compound of step e) at the active groups of the reactivated matrices.

3. A method according to claim 1, wherein the matrices consist of cellulose, polystyrene, polypropylene, polycarbonate or glass.

4. A method according to claim 1, further including the step of reacting the product of step c), having unreacted active groups, with a low molecular weight compound, having active amino groups and containing positively charged, negatively charged, hydrophobic, hydrophilic or amphipathic groups, in an aqueous buffer system, free of primary and secondary amines, at a pH of 7–10 for modulating the biochemical, immunochemical or enzymatic reaction or activity of the matrices.

5. A method for immobilizing biornolecules and affinity ligands, said method comprising the steps of:
   a) dissolving a protein containing at least one primary or a secondary amino group;
   b) reacting the protein of step a) with a cyclobutene carboxylic acid derivative, selected from the group consisting of cyclobutene carboxylic acid diester, cyclobutene carboxylic acid halide, cyclobutene carboxylic acid ester halide, cyclobutene carboxylic acid dialkoxyester, and cyclobutene carboxylic acid imidazole, in methanol in the presence of triethylamine;
   c) adding the product of step b) to water insoluble matrices, having amino groups and being selected from the group consisting of test tubes, microtiter plates, microscope slides, beads, membranes, resins, and filters;
   d) incubating the matrices and the product of step b) at a pH of 7–10 and a temperature of +4° C. to +60° C. in an aqueous buffer system, free of primary and secondary amines, to thereby immobilize the compound of step a) on the matrices.

6. A method according to claim 5, further including the steps of:

e) reacting the matrices of step d) with a cyclobutene carboxylic acid derivative, selected from the group consisting of cyclobutene carboxylic acid diester, cyclobutene carboxylic acid halide, cyclobutene carboxylic acid ester halide, cyclobutene carboxylic acid dialkoxyester, and cyclobutene carboxylic acid imidazole, as an activating compound in methanol in the presence of triethylamine to reactivate the matrices with active groups; and f) dissolving a protein containing at least one primary amino or secondary amino group and adding the protein to the reactivated matrices of step e);

g) incubating the reactivated matrices of step e) with the dissolved compound of step f) at a pH of 7–10 and a temperature of +4° C. to +60° C. in an aqueous buffer system, free of primary and secondary amines, to thereby immobilize the compound of step f) at the active groups of the reactivated matrices.

7. A method according to claim 5, wherein the matrices consist of cellulose, polystyrene, polypropylene, polycarbonate or glass.

8. A method according to claim 5, further including the step of reacting the product of step c), having unreacted active groups, with a low molecular weight compound, having active amino groups and containing positively charged, negatively charged, hydrophobic, hydrophilic or amphipathic groups, in an aqueous buffer system, free of primary and secondary amines, at a pH of 7–10 for modulating the biochemical, immunochemical or enzymatic reaction or activity of the matrices.

9. A method for producing matrices for immobilizing biomolecules and affinity ligands, said method comprising the steps of:

a) reacting water insoluble matrices, having amino groups and being selected from the group consisting of test tubes, microtiter plates, microscope slides, beads, membranes, resins, and filters, with a cyclobutene carboxylic acid derivative, selected from the group consisting of cyclobutene carboxylic acid diester, cyclobutene carboxylic acid halide, cyclobutene carboxylic acid ester halide, cyclobutene carboxylic acid dialkoxyester, and cyclobutene carboxylic acid imidazole, as an activating compound in methanol in the presence of triethylamine to form active matrices with active groups;

b) reacting the activated matrices with a polyamine, containing primary or secondary amino groups, to provide hydrophilic spacer groups;

c) reacting the hydrophilic spacer groups of the matrices resulting from step b) with a cyclobutene carboxylic acid derivative, selected from the group consisting of cyclobutene carboxylic acid diester, cyclobutene carboxylic acid halide, cyclobutene carboxylic acid ester halide, cyclobutene carboxylic acid dialkoxyester, and cyclobutene carboxylic acid imidazole, as an activating compound in methanol in the presence of triethylamine to reactivate the matrices with active groups.

10. A method according to claim 9, wherein the matrices consist of cellulose, polystyrene, polypropylene, polycarbonate or glass.

* * * * *